United States Patent
Sheardown et al.

(10) Patent No.: US 10,611,908 B2
(45) Date of Patent: Apr. 7, 2020

(54) MICELLES FOR MUCOADHESIVE DRUG DELIVERY

(71) Applicant: McMaster University, Hamilton (CA)

(72) Inventors: Heather Sheardown, Nobleton (CA); Graeme Prosperiporta, Calgary (CA); Stephanie Kedzior, Burlington (CA); Benjamin Muirhead, Hamilton (CA)

(73) Assignee: McMaster University, Hamilton, Ontario (CA)

( * ) Notice: Subject to any disclaimer, the term of this patent is extended or adjusted under 35 U.S.C. 154(b) by 54 days.

(21) Appl. No.: 15/756,758

(22) PCT Filed: Sep. 1, 2016

(86) PCT No.: PCT/CA2016/051038
§ 371 (c)(1),
(2) Date: Mar. 1, 2018

(87) PCT Pub. No.: WO2017/035656
PCT Pub. Date: Mar. 9, 2017

(65) Prior Publication Data
US 2018/0265694 A1    Sep. 20, 2018

Related U.S. Application Data

(60) Provisional application No. 62/212,784, filed on Sep. 1, 2015.

(51) Int. Cl.
| | |
|---|---|
| *C08L 53/00* | (2006.01) |
| *C08L 33/04* | (2006.01) |
| *A61K 9/06* | (2006.01) |
| *A61K 47/34* | (2017.01) |
| *A61K 38/00* | (2006.01) |
| *A61K 9/48* | (2006.01) |

(Continued)

(52) U.S. Cl.
CPC ........... *C08L 53/00* (2013.01); *A61K 9/006* (2013.01); *A61K 9/1075* (2013.01); *A61K 47/34* (2013.01); *A61K 49/0043* (2013.01); *A61K 49/0082* (2013.01); *C08F 293/005* (2013.01); *C08L 33/04* (2013.01); *A61K 9/0048* (2013.01); *A61K 38/00* (2013.01); *C08F 2438/03* (2013.01)

(58) Field of Classification Search
CPC ......... C08L 53/00; C08L 33/04; A61K 9/006; A61K 9/1075; A61K 9/0048; A61K 47/34; A61K 38/00; A61K 49/0043; A61K 49/0082; C08F 293/005; C08F 2438/03
USPC ........................................... 524/505
See application file for complete search history.

(56) References Cited

U.S. PATENT DOCUMENTS 6,579,519 B2   6/2003   Maitra et al.
8,242,165 B2   8/2012   Dash et al.
(Continued)

OTHER PUBLICATIONS

Yang et al., Biomacromolecules, 15, Mar. 10, 2014, pp. 1346-1354.*
(Continued)

*Primary Examiner* — William K Cheung
(74) *Attorney, Agent, or Firm* — Gowling WLG (Canada) LLP

(57) ABSTRACT

Biocompatible block copolymer micelles for use in mucoadhesive drug delivery are provided. The micelles comprise a degradable hydrophobic polymer, a degradable synthetic hydrophilic polymer and a mucoadhesive polymer. The micelles are particularly useful for ophthalmic uses.

27 Claims, 7 Drawing Sheets

(51) Int. Cl.
*C08F 293/00* (2006.01)
*A61K 49/00* (2006.01)
*A61K 9/00* (2006.01)
*A61K 9/107* (2006.01)

(56) References Cited

U.S. PATENT DOCUMENTS 9,056,137 B2     1/2015   Hsu
2015/0320694 A1*   11/2015   Gu ........................ A61K 47/26
                                                                  424/499

OTHER PUBLICATIONS

International Search Report of PCT/CA2016/51038 dated Nov. 4, 2016.
Written Opinion of PCT/CA2016/51038 dated Nov. 4, 2016.
Yang, J., et al., Biomacromolecules, 15, Mar. 10, 2014, pp. 1346-1354.
Liu, S., et al., Macromolecular Bioscience, 12, Dec. 2012, pp. 1622-1626.
Liu, S., et al., Nano Research, Jul. 27, 2014.
Liu, L., and Sheardown, H, Investigative Ophthalmology & Visual Science, 55, Apr. 2014, p. 455.

* cited by examiner

MICELLES FOR MUCOADHESIVE DRUG DELIVERY

This application is a national stage filing under 35 U.S.C. § 371 of PCT International Application No. PCT/CA2016/051038, filed Sep. 1, 2016, which claims priority and benefit of U.S. Provisional application Ser. No. 62/212,784 filed Sep. 1, 2015, the contents of both of which are incorporated herein by reference in their entirety.

THE INVENTION

The present invention relates generally to materials for drug delivery, and more particularly to micelles for mucoadhesive drug delivery.

BACKGROUND OF THE INVENTION

The most common method to treat anterior segment diseases of the eye is by topical drop administration due to its low cost, ease of application, and non-invasiveness. Unfortunately, numerous barriers prevent efficient delivery of therapeutics to the anterior segment resulting in less than 5% of the administered dose reaching the anterior tissues in most cases. Static barriers including tight junctions of the conjunctiva, the hydrophobic corneal epithelium and hydrophilic corneal stroma, and dynamic barriers including the rapid tear turnover, and the vasculature and lymphatics of the conjunctiva all contribute to the highly impenetrable anterior surface. Pre-corneal clearance mechanisms such as blinking, rapid tear turnover, and lacrimal drainage are additional barriers even before reaching the anterior tissues that must be overcome. Upon instillation of an eye drop, the maximal 30 µL that can be held in the cul-de-sac is restored to its normal 7 µL tear volume within 2 to 3 minutes resulting in the rapid drainage of 80% or more of the drug through the nasolacrimal duct for systemic absorption and potential side effects.

The tear film itself is composed of an outer lipid layer, a middle aqueous layer containing secreted mucin, and an inner mucin layer immobilized on the glycocalyx covering the corneal and conjunctival epithelium. The inner immobilized mucin layer is thought to act as yet another protective barrier against the diffusion of macromolecules, microbes, and hydrophobic molecules due to its hydrophilic nature. Rose bengal, an anionic dye has been shown to stain corneal epithelium more readily with less mucin showing that mucin has an effect on drug delivery.

One method that has been explored to improve drug transport into ocular tissues has been to utilize mucoadhesive polymers that increase the bioavailability of drug in the immobilized mucin layer. There are many well-known natural mucoadhesive polymers including chitosan, cellulose derivatives, thiomers, and many others, but these materials generally lack the versatility for nanoparticle design to achieve desirable release characteristics. Phenylboronic acid (PBA) is a synthetic molecule that has been extensively used in glucose sensing and insulin delivery systems due to its ability to form high affinity complexes with 1,2-cis-diols. This affinity between boronic acids and diols has also been utilized in other mucoadhesive drug delivery systems such as vaginal delivery of interferon, nasal delivery of insulin, and ocular delivery of cyclosporine A (CycA).

It would be desirable to develop novel methods of delivering cargo, such as therapeutic agents, to mucosal surfaces, including the ocular mucosa.

SUMMARY OF THE INVENTION

Novel mucoadhesive block polymer micelles are herein provided comprising a mucoadhesive component, a degradable component and a micelle-forming component. The micelles are useful for the delivery of cargo to a mucosal surface.

Thus, in one aspect of the invention, biocompatible mucoadhesive block copolymer micelles are provided comprising a degradable hydrophobic polymer, a degradable synthetic hydrophilic polymer and a mucoadhesive component.

In another aspect, a method of delivering cargo to a mucosal surface in a mammal comprising administering to the mammal micelles comprising a degradable hydrophobic polymer, a degradable synthetic hydrophilic polymer and a mucoadhesive component.

In another aspect, a mucoadhesive-based ophthalmic drug delivery system comprising poly(L-lactide)-b-poly(methacrylic acid-co-phenylboronic acid) copolymer micelles is provided.

These and other aspects of the invention are described in the detailed description that follows by reference to the following drawings.

DETAILED DESCRIPTION OF THE INVENTION

Figure 1:
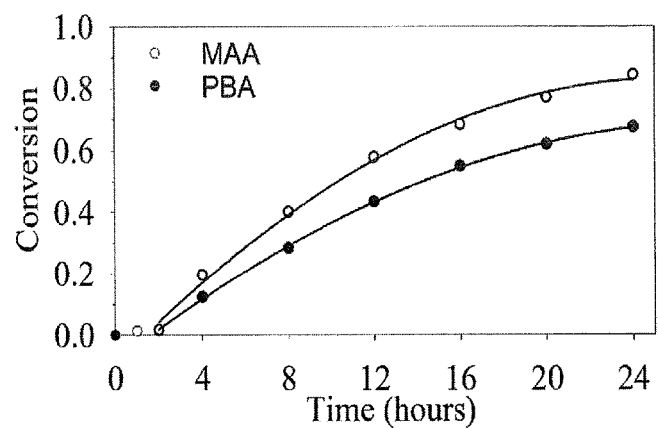
FIG. 1 shows polymerization kinetics of MAA and PBA in the LMP-10 copolymer synthesis.

Novel biocompatible mucoadhesive micelles are herein provided comprising a hydrophobic component, a hydrophilic component and a mucoadhesive component. The micelles are useful for the delivery of cargo, such as a therapeutic agent, to a mucosal surface.

The present mucoadhesive micelles comprise a hydrophobic component that forms the core of the micelles. The hydrophobic component will generally be degradable polymer having a molecular weight in the range of about 0.1 to 2000 kDa, and preferably, 1 to 200 kDa. The hydrophobic component may comprise synthetic hydrophobic polymers such as, but not limited to, polyesters, polyurethanes, polyureas, polycarbonates, polyethers, polysulfides, polysulfonates, polyimides, polybenzimidazoles, and combinations thereof. The hydrophobic polymer may also be a naturally occurring hydrophobic polymer such as a lipoglycan, a proteoglycan, and the like, modified versions thereof, or combinations thereof. Examples of hydrophobic polymers for inclusion in the present micelles, thus, include, but are not limited to, a polylactide, polyglycolide, poly(lacide-co-glycolide, poly(ε-caprolactone), poly-3-hydroxybutyrate, poly(dioxanone), poly(3-hydroxybutyrate), poly(3-hydroxyvalcrate), poly(valcrolactone), poly(tartonic acid), poly(malonic acid), poly(anhydrides), poly(orthoesters), polyphosphazenes and acryloyloxy dimethyl-γ-butyrolactone (DBA) and other lactone-containing polymers, and combinations thereof.

The hydrophilic component forms an outer shell of the present micelles. The hydrophilic component may comprise degradable synthetic hydrophilic polymers comprising reactive entities and having a molecular weight in the range of about 0.1 to 1000 kDA, and preferably, in the range of 1 to 100 kDa. The term "synthetic" is used herein to refer to polymers which are chemically synthesized as opposed to naturally occurring. Examples of suitable synthetic hydrophilic polymers for inclusion in the present micelles, include but are not limited to, polyacrylic acids, polyalcohols, polyacrylates, polyurethanes, polyacrylamines, polyacrylamides, polyethers and polypyrollidones. Thus, suitable hydrophilic polymers may include those comprising one or more monomers selected from acrylate, acrylic acid, methacrylate, methacrylic acid, methyl acrylate, ethyl acrylate, methyl methacrylate, acrylonitrile, 2-chloroethyl vinyl ether, 2-ethylhexyl acrylate, hydroxyethyl methacrylate, butyl acrylate, butyl methacrylate, trimethylolpropane triacrylate, hydroxypropylmethacrylamide, hydroxyethyl acrylate, poly(ethylene glycol) methacrylate, poly(N-isopropylacrylamide) (PNIPAM), poly(vinyl alcohol) (PVA), poly(2-oxazoline), polyethylene glycol, or polyvinylpyrollidone polymers, or copolymers thereof.

The hydrophilic component is linked to a mucoadhesive component which functions to adhere the micelles to a target mucosal surface. The mucoadhesive component is linked to the hydrophilic component via reactive entities on the hydrophilic component. The term "linked" is used herein to refer to covalent linkages, ionic bonds, hydrogen bonds, van der Waals forces, and the like. The reactive entities may naturally exist on or be innate to the hydrophilic component, or may be introduced onto the hydrophilic component. Such reactive entities may include, for example, hydroxyl, amine, thiol, ketone, and carboxylic acid groups.

The mucoadhesive component is selected for its ability to adhere or bind to a mucosal surface, to retain the present micelles at a target mucosal site. Thus, the mucoadhesive component will generally recognize and bind to a constituent of a target mucosal surface, including a glycoprotein such a mucin, a receptor, a polysaccharide or other constituent.

In one embodiment, the mucoadhesive component is capable of binding to mucin. In this regard, the mucoadhesive will be selected to bind to cis-diol groups present in carbohydrates within mucin, e.g. sialic acids, N-acetylglucosamine, N-acetylgalactosamine, galactose and fucose. Examples of a suitable mucoadhesive for this purpose, include, but are not limited to, boronic acids such as phenylboronic acid, 2-thienylboronic acid, methylboronic acid, cis-propenylboronic acid, trans-propenylboronic acid, (4-allylaminocarbonyl)benzeneboronic acid, (4-aminosulfonylphenyl)boronic acid, (4-benzyloxy-2-formyl)phenylboronic acid, (4-hydroxy-2-methyl)phenylboronic acid, (4-hydroxy-2-methyl)phenylboronic acid, (4-methanesulfonylaminomethylphenyl)boronic acid, (4-methanesulfonylaminomethylphenyl)boronic acid, (4-methylaminosulfonyl-phenyl) boronic acid, (4-methylaminosulfonylphenyl)boronic acid, (4-phenylamino-carbonylphenyl)boronic acid, (4-phenylaminocarbonylphenyl)boronic acid, (4-sec-butyl) benzeneboronic acid, (2,6-dimethoxy-4-methylphenyl)boronic acid, (2,6-dimethoxy-4-methylphenyl)boronic acid, (2-methylpropyl)boronic acid, (2-methylpropyl) boronic acid, (3-acetamido-5-carboxy)phenylboronic acid, (3-acetamido-5-carboxy) phenyl boronic acid, (3-acetamidomethylphenyl)boronic acid, (3-acetamidomethylphenyl) boronic acid, (3-allylaminocarbonyl)benzeneboronic acid, (3-cyanomethylphenyl)boronic acid, and derivatives thereof, including boronic esters formed by reaction of boronic acid with an alcohol. Examples of boronic esters include, but are not limited to, allylboronic acid pinacol ester, phenyl boronic acid trimethylene glycol ester, diisopropoxymethylborane, bis(hexyleneglycolato)diboron, t-butyl-N-[4-(4,4,5,5-tetramethyl-1,3,2-dioxaborolan-2-yl)phenyl]carbamate, 2,6-dimethyl-4-(4,4,5,5-tetramethyl1,3,2-dioxaborolan-2-yl)benzoate, 4-(4,4,5,5-tetramethyl1,3,2-dioxaborolan-2-yl)aniline, 4-(4,4,5,5-tetramethyl1,3,2-dioxaborolan-2-yl)benzoic acid, 4-(4,4,5,5-tetramethyl1,3,2-dioxaborolan-2-yl)phenol, 2-methoxy-4-(4,4,5,5-tetramethyl1,3,2-dioxaborolan-2-yl)phenol, and the like.

In another embodiment, the mucoadhesive is selected to bind to cysteine residues in mucin. Examples of such a mucoadhesive include thiol-containing compounds such as cysteamine. In another embodiment, the mucoadhesive is selected to bind to glycoproteins in mucin which contain hydroxyl groups. Suitable glycoprotein-binding mucoadhesives include acrylate compounds such as methacrylate, ethyl acrylate and diacrylate. Other mucoadhesive compounds include natural polymers such as chitosan, cellulose, hyaluronic acid and thiomers such as thiolated chitosan, thiolated hyaluronic acid and thiolated poly(acrylic) acid. Mixtures of mucoadhesive compounds may also be used.

The hydrophobic, hydrophilic and mucoadhesive components are combined to prepare the present micelles using methods established in the art. First, the components are polymerized using methods known in the art of polymer chemistry. In one embodiment, free radical polymerization could be used to prepare the micelles. In another embodiment, a reversible-deactivation radical polymerization may be used, including reversible addition-fragmentation chain transfer (RAFT) polymerization. RAFT polymerization uses thiocarbonylthio compounds, such as dithioesters, thiocarbamates, and xanthates, to mediate the polymerization via a reversible chain-transfer process. Generally, a suitable amount of each of the hydrophobic, hydrophilic and mucoadhesive polymers are combined. One of skill in the art will appreciate that the amounts of each used to make the present micelles will vary with the polymers used. In one embodiment, hydrophobic polymer (e.g. in an amount in a range of about 1-5 molar percent, e.g. about 2 molar percent; hydrophilic polymer (e.g. in an amount in a range of about 75-85 molar percent, e.g. about 80 molar percent; mucoadhesive polymer (e.g. in an amount in a range of about 15-25 molar percent, e.g. about 20 molar percent, and a free radical initiator, are dissolved in an appropriate solvent (which may vary with the polymers used). Dioxane:water, acetone:water and DMSO:water are examples of suitable solvents. Examples of free radical initiators that may be used include halogen molecules, azo compounds such as azobisisobutyronitrile (AIBN), 4,4'-azobis(4-cyanovaleric acid), 1,1'-azobis(cyclohexanecarbonitrile and 2,2'-azobis(2-methylpropionitrile, organic peroxides (e.g. tert-butyl hydroperoxide, dicumyl peroxide and benzoyl peroxide) and inorganic peroxides (e.g. potassium persulfate, sodium persulfate or ammonium persulfate). The solution is then heated with stirring for an appropriate period of time. The resulting mucoadhesive block copolymer may be isolated by precipitation.

Appropriate mucoadhesive block copolymers for use to make micelles in accordance with the invention will have a hydrophobic polymer:hydrophilic polymer:mucoadhesive ratio of about 0.5:94.5:5 to about 5:65:30.

The isolated mucoadhesive copolymer is formed into micelles by precipitation. The polymer is first dissolved in an appropriate solvent, such as acetone, to form a copolymer solution. The copolymer solution is then added to water with constant stirring until the solvent has evaporated. Nano-sized micelles are formed, e.g. less than 500 nm, preferably less than about 200 nm, for example, in the range of about 1-150 nm, e.g. 100, 90, 80, 70, 60, 50, 40, 30 or 20 nm or less. The micelles have a hydrophobic core and a hydrophilic shell incorporating the mucoadhesive component.

The micelles are useful for the delivery of cargo, e.g. therapeutics, to a mucosal surfaces including, but not limited to the ocular mucosa, nasal mucosa, oral mucosa, olfactory mucosa, bronchial mucosa, esophageal mucosa, gastric mucosa, intestinal mucosa, endometrium, penile mucosa, vaginal mucosa and anal mucosa. Micelles containing cargo are readily prepared by dissolving the mucoadhesive copolymer in a solvent comprising the cargo, and adding the solution to water with stirring to form the micelles as described above. Generally the micelles are loaded with an amount of cargo in the range of 5-50% by weight of the micelles.

As one of skill in the art will appreciate, the micelles may include various types of cargo, including therapeutic agents, diagnostic agents and the like. The cargo may be small molecules, or larger compounds such as proteins, nucleic acids, carbohydrates, or the like. Examples of therapeutic agents that may be loaded into the present micelles include analgesics, anti-inflammatory agents, anti-pathogenic agents including antibacterial, antiviral and antifungal agents, gastrointestinal agents, anti-histamines, anti-allergic agents, anti-cancer agents, anti-nauseants, anti-asthmatic agents, decongestants, glaucoma medication, intra-ocular pressure lowering drugs (IOP-lowering agents), lubricants, demulcents, counter-irritants, hypertonic tears, as well as therapeutic, diagnostic, and anti-ototoxic agents applied to the inner ear.

Preferred therapeutic agents are those which treat a condition within the proximity of a mucosal site. Examples include ophthalmic drugs such as cyclosporine A, acyclovir, atropine, acetazolamide, alphagan, azithromycin, bacitracin, betadine, betaxolol, betoptic, brinzolamide, carbachol, cefazolin, celluvisc, chloramphenicol, ciloxan, ciprofloxacin, cephalosporin, emecarium, dexamethasone, dipivefrin, dorzolamide, epinephrine, erythromycin, fluorescein, flurbiprofen, quinolones such as fluoroquinolone, gentamicin, goniosol, gramicidin, gancyclovir, gatafloxacin, humorsol, hylartin, itraconazole, ketotifen, latanoprost, levofloxacin, bimatoprost, travoprost, pilocarpine, polymyxin B, prednisolone, proparacaine, propine, puralube, mannitol, methazolamide, miconazole, miostat, moxifloxacin, natamycin, neomycin, neptazane, ocuflox, ofloxacin, oxytetracycline, olopatadine, phenylephrine, prostaglandin, sodium hyaluronate, suprofen, terramycin, timolol, tobramycin, triamcinolone, trfluridine, tropicamide, vidarabine, valcyclovir, vancomycin, xalatan, phenylephrine, prostaglandins and anti-VEGF drugs such as ranibizumab and pegaptanib sodium.

Examples of therapeutic agents for delivery to other mucosal sites include, but are not limited to, methylprednisolone targeted to the mastoid mucosa of the middle ear to treat Meniere's Disease; clotrimazole delivered to the vaginal mucosa to treat yeast infections; balsalazide targeted to the intestinal mucosa to treat inflammatory bowel disease; ipratropium delivered via inhaler to the lung for acute asthma, and azelastine delivered via nasal spray to reduce allergic irritation. As one of skill in the art will appreciate, a therapeutic agent targeting any tissue with an associated mucosal membrane that is susceptible to dysfunction or disease may be delivered using the present micelles.

Examples of diagnostic agents that may be delivered to a mucosal site using the present micellar delivery system include contrast agents such as gadolinium chelates, iron, magnesium, manganese, copper and chromium, imaging agents such as iodine-based agents and fluorescent molecules, and radionucleotides such as gamma-emitters, positron-emitters and X-ray emitters.

The present micelles may be formulated for administration by various routes, including oral, intranasal, enteral, topical, sublingual, intra-arterial, intramedullary, intrauterine, intrathecal, inhalation, ocular, transdermal, vaginal, rectal, infusion or injection, e.g. subcutaneously, intraperitoneally, intramuscularly or intravenously.

The present micelles, thus, may be combined to form a composition with one or more pharmaceutically acceptable carriers and/or excipients to facilitate their delivery to a target mucosal site. The expression "pharmaceutically acceptable" means acceptable for use in the pharmaceutical and veterinary arts, i.e. not being unacceptably toxic or otherwise unsuitable. Examples of pharmaceutically acceptable adjuvants are those used conventionally with micelle-based drugs, such as diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated as a gel, solution, or ointment for topical administration to the eye or ear. Such topical formulations may include fats, oils, waxes, polyethylene glycol, silicone, silicic acid, zinc oxide, starch, and cellulose derivatives. Creams, lotions and ointments may be prepared for transdermal application using an appropriate base such as a triglyceride base, or one or more of fats, oils, waxes, polyethylene glycol, silicone, silicic acid, zinc oxide, starch, and cellulose derivatives. Such creams, lotions and ointments may also contain a surface active agent. Creams, lotions and ointments may be formulated as a suppository for rectal or vaginal administration. Aerosol formulations for administration nasally may also be prepared in which suitable propellant adjuvants are used.

For oral administration via tablet, capsule or suspension, the present micelles may be combined with adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitoL and polyethylene glycol; agar; alginic acids; water; isotonic saline and phosphate buffer solutions. Wetting agents, lubricants such as sodium lauryl sulfate, stabilizers, tableting agents, antioxidants, preservatives, colouring agents and flavouring agents may also be present. Other adjuvants may also be added to the composition regardless of how it is to be administered, for example, anti-microbial agents may be added to the composition to prevent microbial growth over prolonged storage periods.

The present micelles are administered in the treatment or diagnosis of a condition at a target mucosal surface or site in an amount sufficient to deliver an effective dosage of therapeutic or diagnostic cargo to the target surface or site. Effective dosages of such cargo, as exemplified herein, would be known to those of skill in the art and may correspond to dosages administered via other delivery systems. Thus, for example, for the delivery of an ophthalmic drug, dosages for use with the present micelles will correspond with dosages generally used in the art. Alternatively, the effective dosage may be reduced from that administered via other delivery systems. For example, CycA is typically administered in excess via ~500 µL aliquot containing 0.05% CycA dropped onto the ocular surface twice daily. However, this micelle technology represents a fundamental departure from this paradigm. Given the mucoadhesion and controlled release provided by the present micelles, dosing frequency and total amount of CycA required to achieve therapeutic effect may be reduced. In one embodiment, a single drop (0.05 mL) at 5 mg/mL CycA provided once per week may be used.

The present micelles, including an appropriate therapeutic or diagnostic agent, may be administered to a target mucosal surface in a method to treat or diagnose various pathogenic conditions such as conditions affecting the eye, nose, mouth, ear, throat, esophagus, stomach, intestines, endometrium, penis, vagina or anus. Such conditions may include, but are not limited to, infection, inflammation, cancer, degenerative disease, allergic reaction, injury, scarring and the like.

In one embodiment, the present micelles are used in the treatment of a condition affecting the eye. Such conditions may include, but are not limited to, infections, glaucoma, cataracts, diabetic retinopathy, macular dystrophy, dry eye disease, keratoconus, lymphoma, allergies, inflammation, occlusions, hypertension, nystagmus, macular degeneration, cornea transplant, vitamin A deficiency, dendritic ulcer, cysts, scarring, and abrasions.

The present micelles advantageously provide a delivery system that effectively targets mucosal sites for delivery of cargo, such as therapeutic or diagnostic agents, thereto. Due to the inclusion of a synthetic hydrophilic component, the micelles exhibit good stability and can be tailored to achieve optimal delivery of selected cargo to a target mucosal site. The use of a synthetic hydrophilic component may also provide micelles which are non-immunogenic.

Embodiments of the invention are described in the following specific examples which are not to be construed as limiting.

Example 1

Materials—Unless otherwise stated, all materials were purchased from Sigma Aldrich (Oakville, ON, Canada) and used as received. 3-acrylamidophenylboronic acid was purified by recrystallization in water. Azobisisobutyronitrile (AIBN) was purified by recrystallization in methanol. 1,4-dioxane, tetrahydrofuran, diethyl ether, N,N-dimethylformamide, and acetonitrile were purchased from Caledon Laboratories (Caledon, ON) and used as received. DMSO-d6 was purchased from Cambridge Isotope Laboratories Inc. (Andover, Mass. USA) and used as received. Purified water with a resistivity of 18.2 MΩ cm was prepared using a Milli-pore Barnstead water purification system (Graham, N.C. USA). Phosphate buffered saline (PBS) was purchased from BioShop (Burlington, ON, Canada). Cellulose dialysis membranes with molecular weight cut-off (MWCO) values of 3.5 and 50 kDa were purchased from Spectrum Laboratories Inc. (Rancho Dominguez, Calif. USA). 3-[4,5-dimethylthiazol-2-yl]-2,5-diphenyl-tetrazolium bromide (MTT), calcein AM, and ethidium bromide were purchased from Life Technologies (Carlsbad, Calif. USA) and were used as received.

pLA-b-p(MAA-PBA) copolymer synthesis and characterization—pLA-b-p(MAA-PBA) (LMP) copolymers were synthesized by RAFT polymerization. In a typical reaction procedure (80:20:1.4:0.2 molar feed ratio of MAA:PBA: pLA:AIBN), methacrylic acid (MAA; 192.9 mg, 2.24 mmol), PBA (107.1 mg, 0.56 mmol), poly(L-lactide) 4-cyano-4-[(dodecylsulfanylthiocarbonyl)sulfanyl] pentoate (pLA-CDP; 200.0 mg, 0.04 mmol), AIBN (1.10 mg, 0.01 mmol) were dissolved in 5 mL of 90:10 1,4-dioxane:water to form a 10% solution. The solution was degassed by performing three freeze-pump-thaw cycles followed by replacement of the atmosphere with dry nitrogen. The flask was then heated to 70° C. for 24 hours under constant stirring. This copolymer, denoted LMP-20 (20 wt. % PBA in the poly(MAA-co-PBA) block) was isolated by precipitation into 10 times excess of cold anhydrous diethyl ether and further purified by repeated precipitation into diethyl ether from tetrahydrofuran. The copolymer was dried in a vacuum oven at 50° C. for 24 hours until constant weight had been achieved.

LMP copolymer composition and molecular weight were determined using $^1$H NMR (Bruker AV 600) in DMSO-d6. LMP polymerization kinetics were studied to determine the distribution of PBA within MAA-PBA block and controlled nature of polymerization. Polymerization was performed as previously stated although at specified time points a nitrogen purged airtight needle was used to remove 50 µL samples for proton nuclear magnetic resonance ($^1$H NMR; Bruker AV 600) in DMSO-d6.

Micelle Formation and Characterization—Micelles were formed by the precipitation method. 20 mg of LMP copolymer was dissolved in 2 mL acetone. The copolymer solution was added drop-wise to 6 mL of purified water under constant stirring. The acetone/water solutions were then allowed to stir uncovered at room temperature for 48 hours to evaporate the acetone before further characterization. Micelle size was determined using a NanoSight LM10 single nanoparticle tracking instrument (Malvern Instruments Ltd.). Micelle solutions in purified water were diluted to $5 \times 10^{-2}$ mg mL$^{-1}$ before measurement in pH 7.4 PBS. Micelle stability was assessed using Zeta potential (ZetaPlus Analyzer, Brookhaven) in pH 7.4 PBS with 10 mM NaCl. Zeta potential was measured for 1 mg mL$^{-1}$ LMP.

The critical micelle concentration (CMC) was determined using the pyrene fluorescent probe method. A predetermined amount of pyrene was dissolved in acetone and added to 2 mL vials and allowed to evaporate. Micelle solutions ranging from 10 mg mL$^{-1}$ to 10$^{-5}$ mg mL$^{-1}$ were added and incubated for 24 hours at room temperature resulting in final pyrene concentrations of $6.0 \times 10^{-7}$ mol $L^{-1}$. Fluorescence was measured using a TECAN M1000 Pro plate reader (Männedorf, Switzerland). The excitation spectrum was measured after an excitation wavelength of 340 nm. The CMC was determined by plotting the intensity ratio of peaks at 373 nm to those at 383 nm against the logarithm of concentration. The emission and excitation bandwidths for all measurements was 5 nm.

Mucoadhesion by Surface Plasmon Resonance—Mucoadhesion was determined using Surface Plasmon Resonance (SPR; SPR Navi™ 200, BioNavis). Briefly, SPR102-AU gold sensors were cleaned using piranha (3:1 94% sulfuric acid:hydrogen peroxide), rinsed extensively with purified water and dried under a stream of nitrogen. These sensors were then incubated in 100 µL of 100 µg $mL^{-1}$ bovine submaxillary gland mucin for 24 hours at 20° C. and then rinsed with purified water to remove unbound mucin. SPR measurements were conducted by flowing simulated tear fluid (STF; 23.1 mM KCl, 20.0 mM $NaHCO_3$, 1 mM $CaCl_2.2H_2O$, 113.5 mM NaCl) for 10 minutes to achieve a stable baseline. The solution was then changed to a 1 mg $mL^{-1}$ solution of chitosan or LMP micelles for 50 minutes. At this point, the solution was changed back to simulated tear fluid to assess mucoadhesion stability. All measurements were conducted at a flowrate of 50 µL $min^{-1}$, a temperature of 22° C., and a fixed angle scan of 65.4°.

Cyclosporine A (CycA) Release—CycA release from micelles was determined using high performance liquid chromatography (HPLC). Briefly, a 20 mg of the LMP copolymer was dissolved in 2 mL of acetone containing 1.5 mg $mL^{-1}$ CycA. This solution was added drop-wise to 6 mL of purified water. The solution was left under stirring for 24 hours to evaporate the acetone. 0.5 mL was removed and filtered with Nanosep 10K Omega centrifugal units (10 kDa MWCO, Pall Corporation) to separate micelles from free CycA. The filtrate was collected to determine entrapment efficiency (EE). 5 mL of non-centrifuged sample was then added to 50 kDa MWCO dialysis tubes and placed in 15 mL of STF. At specified time points, 2.5 mL samples were removed and replaced with fresh pre-warmed STF. These samples were analyzed using a Waters HPLC consisting of a 2707 autosampler, 2489 UV spectrophotometer, 1525 binary HPLC pump, and Breeze 2 software (Build 2154). A 0.7 mL $min^{-1}$ isocratic flow rate of 80:20 acetonitrile:0.1% trifluoroacetic acid in purified water as the mobile phase, a 60° C. column temperature, a 20 µL sample injection volume, and a 210 nm detection wavelength were used. Sample concentrations were determined based on a standard calibration curve of CycA in the mobile phase.

Cell Culture—For cell culture, all copolymers were extensively dialyzed in 2:1 acetone:water solutions against 3.5 kDa MWCO dialysis tubing to prevent micelle formation followed by the transition to purified water and then were freeze dried. 50 mg of copolymer was then dissolved in 1 mL of acetone and added dropwise under constant stirring to 2.5 mL of sterile water. The acetone was allowed to evaporate for 48 hours under constant stirring whereby concentrated PBS and penicillin/streptomycin were added to final concentrations of 0.1 M and 1% (v/v), respectively.

Human corneal epithelial cells (HCECs) were cultured in keratinocyte serum-free media (KSFM) supplemented with bovine pituitary extract (BPE, 0.05 mg/mL) and epidermal growth factor (EGF, 0.005 mg $mL^1$). HCECs were seeded in 96 well plates at densities of 5,000 cells $well^{-1}$ and incubated in a temperature controlled $CO_2$ incubator (37° C., 5% $CO_2$, 95% air, 100% humidity). After 24 hours of growth, the media was replaced with 150 µL of KSFM and either 50 µL of PBS, 20 mg $mL^{-1}$ LMP micelles, or 4 mg $mL^{-1}$ micelles for final LMP micelle concentration of 0, 5, and 1 mg $mL^{-1}$. The plates were incubated at 37° C. at which point cell viability was assessed using an MTT assay, and live/dead cell counts were determined by a calcein AM (CalAM)/ethidium homodimer-1 (EthD-1) assay after 24 and 72 hours.

Statistical Analysis—A one-factor analysis of variance (ANOVA) was used to analyze the micelle size, Zeta potential, and HCEC viability using $\alpha=0.05$ with Tukey post hoc. Statistical analysis was performed using IBM SPSS Statistics V22.0 statistical software (IBM Corp, Armonk, N.Y. USA). All error bars represent standard deviation.

Results

Copolymer Characterization—$^1$H NMR was used to determine the molar composition and the number average molecular weight of the LMP copolymers. According to Table 1, final compositions were determined to be consistent with feed ratios, and molecular weight was similar to the theoretical molecular weight based on reactant ratios.

TABLE 1

LMP block copolymer polymerization data.

| | Molar Feed Ratio (pLA-CDP:MAA:PBA) | $MAA^a$ Conversion | $PBA^a$ Conversion | Final Composition$^a$ (pLA:pMAA:pPBA) | $Mn^a$ (Da) |
|---|---|---|---|---|---|
| pLA-CDP | — | — | — | 100:0:0 | 4711 |
| LMP-0 | 44.3:55.7:0 | 0.80 | — | 49.8:50.2:0 | 10388 |
| LMP-5 | 45.8:51.5:2.7 | 0.88 | 0.65 | 49.4:49.6:1.9 | 10741 |
| LMP-10 | 47.2:47.5:5.3 | 0.87 | 0.66 | 51.3:46.7:3.8 | 10554 |
| LMP-20 | 49.8:40.2:10.0 | 0.89 | 0.68 | 53.9:41.7:7.4 | 10459 |
| LMP-30 | 52.1:33.5:14.4 | 0.84 | 0.65 | 58.1:35.2:10.4 | 10007 |

$^a$Composition in mol. %, conversion, and molecular weight determined by $^1$H NMR.

Due to the amphiphillic properties of the LMP copolymer as well as the affinity of unprotected phenylboronic acid, gel permeation chromatography did not give representative results. For this reason, a kinetic study was performed to better understand the polymerization process and the distribution of phenylboronic acid in the hydrophilic block, shown in FIG. 1. This kinetic study did not show a zero order relationship between conversion and time, which is expected for well controlled RAFT polymerization. Therefore, it is likely that the polydispersity will be higher than traditional RAFT polymerization. The kinetics also show that during the initial stages of polymerization, MAA reacts faster than the PBA, but after 12 hours they achieve a similar polymerization rate. This causes two results: the final copolymer composition has a higher MAA/PBA ratio then the feed ratio, and the distribution of PBA increases during the course of polymerization to produce a gradient within the poly (MAA-co-PBA) segment. The PBA gradient may be beneficial to mucoadhesion because more PBA will be located at the surface to interact with mucin.

Figure 2:
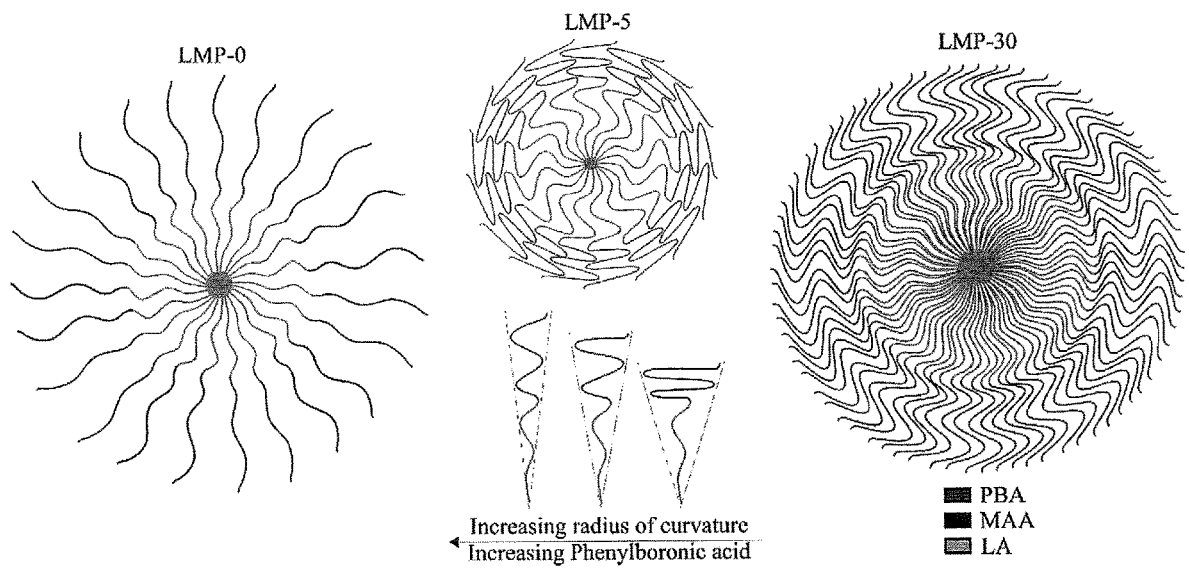
FIG. 2 shows proposed structural changes in LMP copolymer micelles.

Micelle Morphology—Using NanoSight and Zeta potential, the effect of PBA on micelle size and structure, depicted in FIG. 2 was hypothesized. Due to MAA's pKa of ~4.6 and PBA's pKa of ~8.8, the majority of MAA groups should be negatively charged while most of the PBA groups should be uncharged in pH 7.4 PBS [27]. Based on micelle diameter, shown in Table 2, two trends can be seen.

TABLE 2

Size determined using NanoSight of LMP block copolymer micelles.
All reported measurements represent diameter ± SD in nm.

|  | PBS (pH 7.4) | CycA loaded (PBS pH 7.4) |
| --- | --- | --- |
| LMP-0 | 124 ± 43 | 129 ± 49 |
| LMP-5 | 108 ± 68 | 113 ± 46 |
| LMP-10 | 114 ± 95 | 117 ± 48 |
| LMP-20 | 130 ± 78 | 180 ± 86 |
| LMP-30 | 282 ± 118 | 252 ± 103 |

Firstly, as the ratio of PBA/MAA increases in LMP micelles containing PBA, the diameter increases. Secondly, the LMP-0 micelles are larger than LMP micelles containing minimal amounts of PBA. These results can be explained by the presence of two competing forces: intermolecular interactions between negatively charged MAA and water, and inter- and intra-molecular hydrophobic interactions induced by the PBA. The negatively charged MAA groups on the LMP-0 copolymer do two things: they electrostatically repel each other, and they form electronic interactions with water molecules. These effects form a large hydrated outer shell, which contributes to the large diameter. The addition of a small amount of PBA into the outer shell causes the expulsion of some of these water molecules, which causes the outer shell to become less hydrated and smaller. However, as the fraction of PBA is increased further, water expulsion occurs allowing for increased hydrophobic interactions between polymer chains leading to closer packing. Also, the large bulky phenyl ring creates intramolecular steric hindrance within the poly(MAA-co-PBA) polymer chain, creating a more rigid polymer unable to bend and fold into a bulky structure. The increased rigidity allows the hydrophilic poly(MAA-co-PBA) polymers to pack closer together resulting in a larger effective radius of curvature, which increases micelle diameter.

Figure 3:
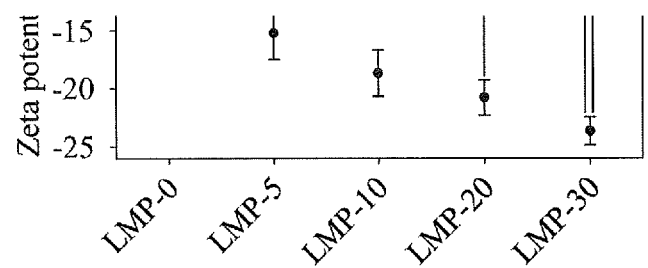
FIG. 3 shows zeta potential of LMP micelles at pH 7.4. Measurement was performed at 1 wt. % micelles. *$p \leq 0.05$, $p \leq 0.01$, *$p \leq 0.001$. All other comparisons were not significantly different ($p \geq 0.05$)

Zeta potential, shown in FIG. 3, had similar trends to the micelle size. LMP micelles containing PBA showed that micelles became more negatively charged as PBA composition was increased. Although initially it seems counterintuitive that increasing the composition of neutral PBA would result in more negatively charged micelles, the change can be explained by charge density rather than total charge. As previously discussed, the LMP polymers with higher PBA compositions pack more closely together due to hydrophobic interactions and steric hindrance. The increased packing results in the greater surface charge measured by zeta potential.

Figure 4:
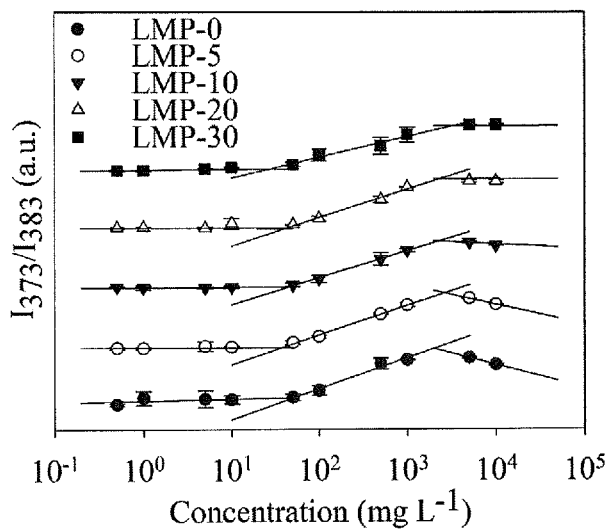
FIG. 4 shows critical micelle concentration for LMP copolymers in PBS (pH 7.4) determined from the ratio of fluorescent intensity at 373 nm to 383 nm after excitation at 340 nm.

Characteristic micelle properties were confirmed by CMC and TEM. TEM characterization showed circular morphology indicative of spherical micelles. All LMP micelles show relatively monodispersed diameters of less than 100 nm in their dry state. CMC was used to characterize the concentration at which micelles begin to form from free block copolymers in solution. The CMC, shown in FIG. 4, was determined for LMP-0, 5, 10, 20, and 30 copolymers to be 73.0, 47.8, 40.6, 41.0, and 32.5 mg mL$^{-1}$ respectively. The slight decreasing trend in CMC with increasing PBA composition can be explained by block copolymer solubility and micelle stability differences. Increasing the PBA composition makes the poly(MAA-co-PBA) block less water soluble, which reduces the driving force for it to enter into solution. Additionally, the hydrophobic interactions between PBA in the outer shell increase the micelle stability by slightly locking it into place preventing the release of block copolymer into solution.

Figure 5:
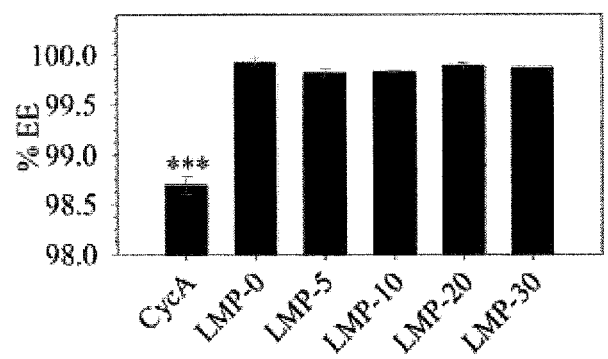
FIG. 5 shows entrapment efficiencies of LMP copolymers and CycA control.***$p<0.001$ compared to all LMP copolymers. All other comparisons were not significant $p>0.05$.
Figure 6:
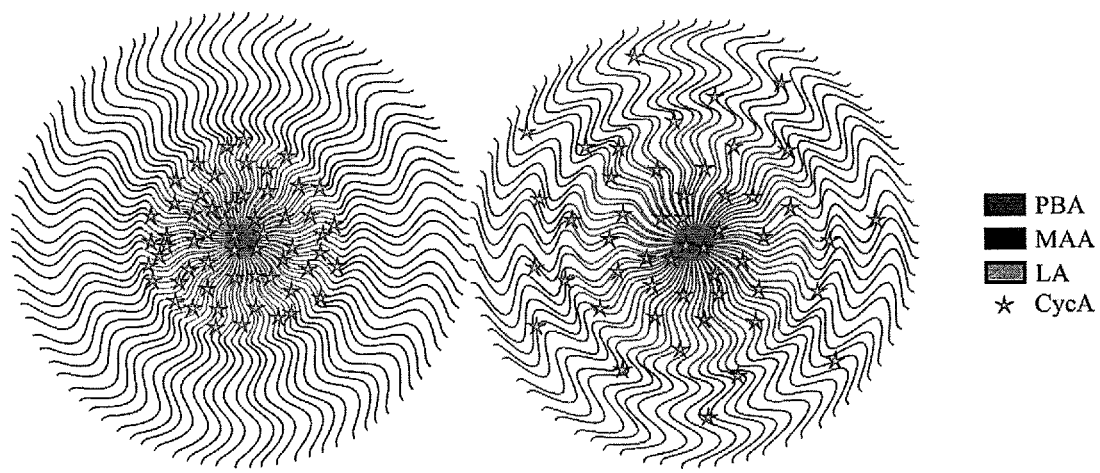
FIG. 6 shows proposed CycA loading distribution in LMP copolymers with varying amounts of PBA.

Cyclosporine A Release—CycA was entrapped within the LMP micelles by dissolving both components in acetone followed by the drop-wise addition into purified water at a ratio of 20 mg copolymer to 3 mg CycA. Upon evaporation of the acetone under constant stirring for 24 hours, the drug loaded micelles were filtered to determine the % entrapment efficiency (EE). FIG. 5 shows the EEs for LMP copolymers as well as a control CycA formulation. All LMP micelles showed EEs greater than 99.8% while the CycA formulation had significantly smaller EE of 98.7%, which represents the maximum solubility of CycA in water. This shows that LMP micelles are very efficient at entrapping CycA, which may reduce the initial undesirable burst release upon application. CycA-loaded LMP micelles had varying transparencies. LMP-0/5/10 micelles were nearly transparent while the LMP-20 and LMP-30 loaded micelles form opaque suspensions. This is likely due to the distribution of CycA in the micelle, which is represented in FIG. 6. The LMP-20/30 micelles contain a significant amount of hydrophobic PBA in the outer hydrophilic shell, which increases the distribution of CycA throughout both the core and shell of the micelle causing changes in the micelle's refractive index. The LMP-0/5/10 micelles however have most of the CycA loaded within their hydrophobic poly(lactide) core and minimal loaded in the outer hydrophilic shell resulting in minimal refractive index changes. These hydrophobic distributions within the micelle also show an effect on the drug release characteristics of these micelles.

Figure 7:
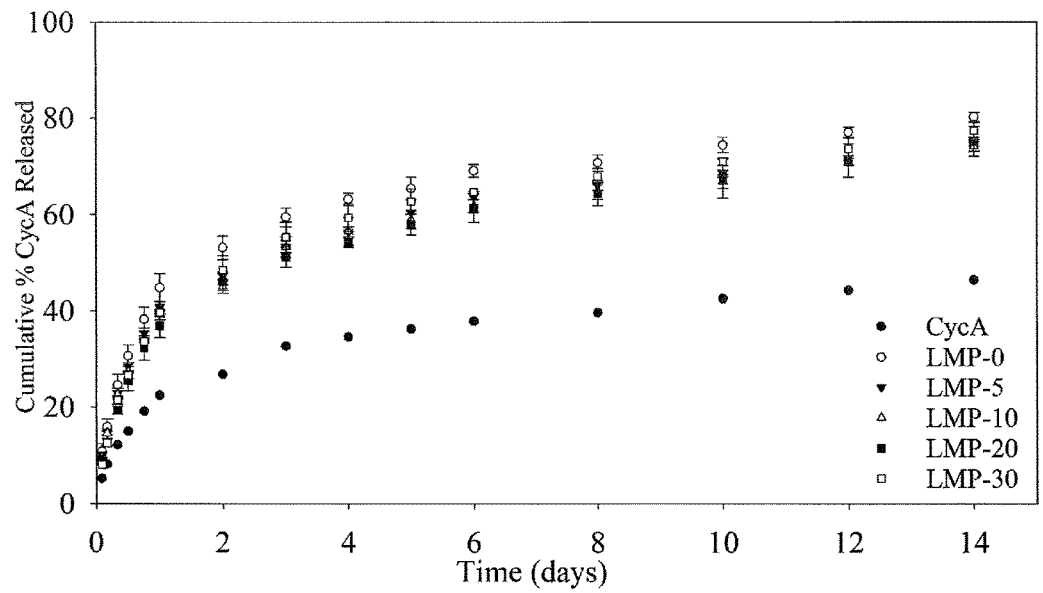
FIG. 7 shows cumulative CycA release from LMP micelle.

Interestingly, all LMP copolymers showed increased release compared to CycA in STF, shown in FIG. 7. This increased release is likely due to free block copolymer diffusion across the 50 kDa MWCO dialysis membrane carrying with it CycA in the hydrophobic poly(lactide) block, which is more indicative of in vivo conditions where there would be no barriers to individual block copolymer diffusion. All LMP copolymers showed a two phase release profile characterized by an initial burst phase lasting approximately 24 hours resulting in 35 to 45% release followed by a non-linear release of between 74 to 80% after 14 days depending on composition. During the initial burst release, the release rate was higher for micelles with lower PBA composition. This can be attributed to the higher CycA loading within the micelle core and the smaller micelle diameter, which results in a larger concentration gradient and shorter diffusion distance causing faster release compared to high PBA micelles, which are larger and have CycA distributed throughout the micelle core and shell. After the initial burst release, the concentration gradient is reduced, which allows the CycA diffusivity across the outer shell to dominate the release characteristics. Micelles with higher PBA composition will have more hydrophobic outer shells, which would increase the diffusivity of CycA from the micelle causing faster release compared to micelles with lower PBA. The removal of organic solvent prior to drug release shows more realistic drug release profiles.

Figure 8:
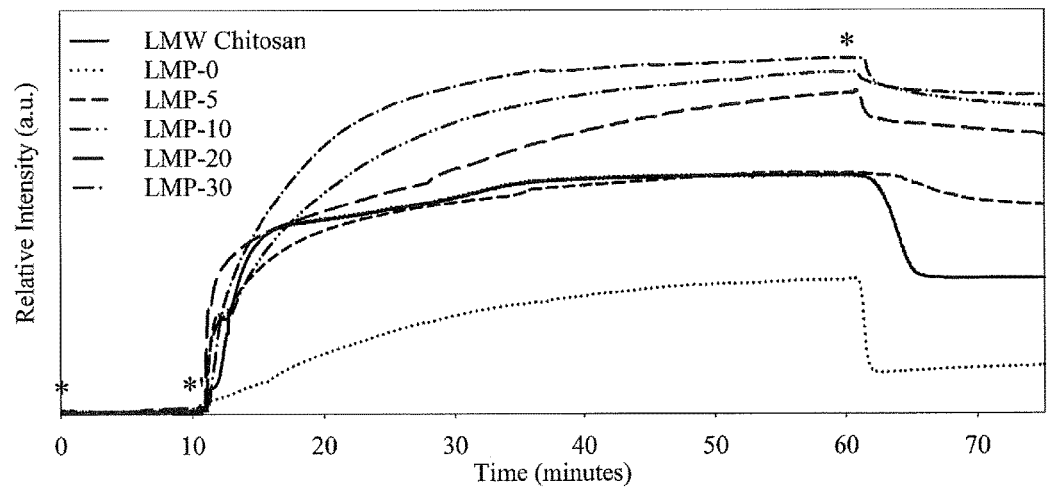
FIG. 8 shows an SPR sensorgram of LMP micelles. STF and LMP represents the flow of simulated tear fluid and LMP micelles, respectively.

Mucoadhesion of LMP copolymers was studied using SPR with chitosan as a positive control for mucoadhesive comparison. FIG. 8 shows the single angle SPR sensorgram for chitosan and the LMP copolymers. It can be seen from this figure that mucoadhesion of the LMP micelles increases with increasing PBA content, but appears to reach a ceiling whereby additional PBA does not greatly increase mucoadhesion. This ceiling effect is likely due to saturation of the mucin monolayer whereby no additional LMP polymers are able to adhere to the surface, which is representative of in vivo conditions. This suggests that higher PBA compositions, which are not transparent, may not be beneficial to in vivo applications. The LMP-10/20/30 micelles all reached a significantly higher relative intensity compared to the chitosan and the LMP-0/5 micelles, which represents greater mucoadhesion. The LMP-0 micelles show the lowest mucoadhesion, which was expected. As with the chitosan, they also showed a greater reduction in relative intensity after the washing step compared to the PBA containing micelles. This reduction represents the stability of the adsorbed layer. This is likely due to the stronger bonding between PBA and sialic acid diols compared to the LMP-0 micelles which forms hydrogen bonds and chitosan which forms electrostatic and hydrogen bonds. PBA containing LMP micelles show significant in vitro mucoadhesion, which has the potential to improve bioavailability of topically applied drugs.

Figure 9:
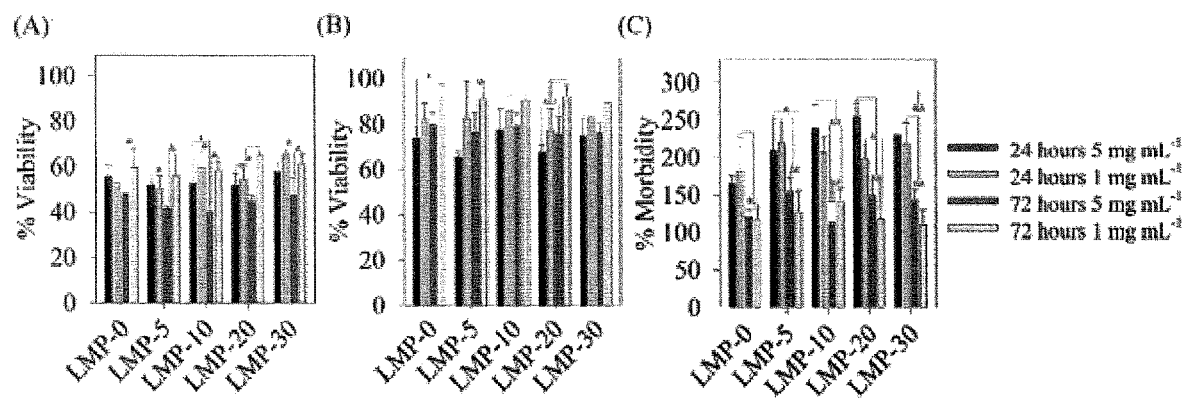
FIG. 9 shows HCEC Viability by A) MTT assay, B) CalAM, and C) EthD-1.

HCEC Viability—To test in vitro cell viability, LMP micelles were incubated with HCECs at concentrations of 1 mg mL$^{-1}$ and 5 mg mL$^{-1}$ for 24 and 72 hours. At each time point, cell metabolic activity was determined using an MTT assay, and live/dead cell counts were determined using CalAM/EthD-1 assays, respectively. It can been seen, from the MTT assay results, (FIG. 9A) that cell metabolism is reduced compared to controls. It also shows a trend that after 72 hours the metabolism of HCECs incubated with 1 mg mL$^{-1}$ micelles is significantly higher than those incubated with 5 mg mL$^{-1}$ micelles. The viability, determined from fluorescent CalAM staining, (FIG. 9B) showed that viability was higher after 72 hours compared to 24 hour samples. This suggests that micelles are not cytotoxic, but rather inhibit growth. CalAM fluorescence also showed that viability was higher for 1 mg mL$^{-1}$ micelles compared to the 5 mg mL$^{-1}$ micelles. The EthD-1 assay (FIG. 9C) showed less than three times morbidity for all micelles compared to controls, which suggests that LMP micelles are not significantly cytotoxic. The EthD-1 assay also showed a trend that % morbidity was significantly lower after 72 hours compared to 24 hours, which may be due to control cells reaching confluence which initiates cell death while the slower growing HCECs containing micelles had not. Interestingly, HCECs cultured with PBA-containing micelles show dense clusters of cells rather than even spreading as seen in the micelles not containing PBA and the controls. The PBA micelles could be mediating cell-cell adhesion by interacting with cell surface mucins, which prevents them from spreading on the plate. It is not believed that inhibition of cell growth seen with these LMP micelles will affect corneal cells in vivo for two reasons: the concentration of LMP micelles on the corneal surface will be lower than those tested due to the rapid tear turnover upon topical administration of eye drops, and the anterior layer of corneal cells is not actively dividing so the reduced in vitro proliferation may not translate to in vivo conditions. The cell viability results show that these PBA-containing micelles are not cytotoxic, but do inhibit HCEC growth and cause cell clustering instead of spreading across the plate.

Conclusions

Mucoadhesive micelles offer significant potential to increase the bioavailability of topically applied drugs to mucosal surfaces, such as ophthalmic drugs. This will help to decrease the dosage, frequency of dose, and off-target systemic toxicity that are commonly associated with topical drops. A series of poly(L-lactide)-b-poly(methacrylic acid-co-phenylboronic acid) copolymer micelles with varying amounts of phenylboronic acid were synthesized by reversible addition-fragmentation chain-transfer polymerization. These micelles have shown improved mucoadhesion compared to commonly known mucoadhesive chitosan with the ability to improve the delivery of a drug, e.g. cyclosporine A. Cell viability showed changes to cell proliferation and morphology, but did not show significant cytotoxicity suggesting the safe translation to in vivo conditions. This simple method to synthesize mucoadhesive micelles offers significant potential to improve the bioavailability of topically applied drugs to mucosal surfaces to treat disease.

Example 2

This experiment was conducted to confirm that the present micelles exhibit mucoadhesion in an in vivo setting.

Micelles containing 20% PBA were modified covalently with 5-aminofluorescein (FA) using carbodiimide-mediated coupling. In a typical reaction procedure, copolymer was dissolved in dry dimethyl sulfoxide in a sealed flask containing a stir bar and covered in aluminum foil to avoid exposure to light. To this solution, 5-aminofluorescein, N,N'-Dicyclohexylcarbodiimide, and 4-Dimethylaminopyridine were added to achieve molar ratios of 100:30:110:10 for MAA groups:FA:DCC:DMAP, respectively. The flask was sealed with a rubber stopper and left to stir for 24 hours. After 24 hours of reaction, the solution was dialysed until sufficiently pure. A single 50 µL drop with 5 mg/mL of micelle was dropped into the eye of a healthy rat. After a single instillation, micelles containing 0% PBA showed no fluorescein staining after 1 hour, while micelles containing 20% PBA were clearly visible after 1 hour, confirming ocular surface binding of PBA-containing micelles in an in vivo environment.

Example 3

To confirm the present micelles are suitable for use in vivo, a preclinical DED model was used in which DED was induced using the caustic chemical agent, benzalkonium chloride (BAC) (as described in Xiong et al., Cornea, May 2008).

Figure 10:
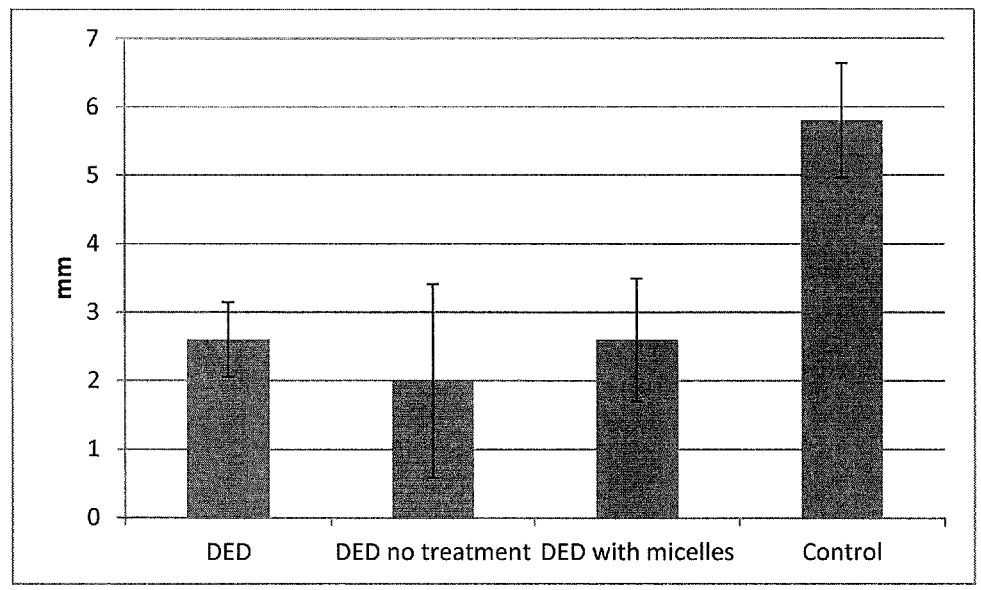
FIG. 10 graphically illustrates the effect of micelles on tear volume in vivo in a DED rat model.

First, it was determined what effect, if any, micelles without drug had on this DED model using the Schrimer's test in which paper test strips with graded markings wick up tear film and determine tear volume. Using the Schrimer's test modified for use in rats (i.e. test strips designed for humans were cut into thirds so each strip was only ⅓ as wide) tear volumes from DED rats after 'treatment' with micelles for 5 days (DED with micelles) were not found to be significantly different to tear volumes from untreated DED rats immediately following DED induction and after 5 days as shown in FIG. 10. Non-DED animals exhibited significantly greater volume of tear film (Control).

Figure 11:
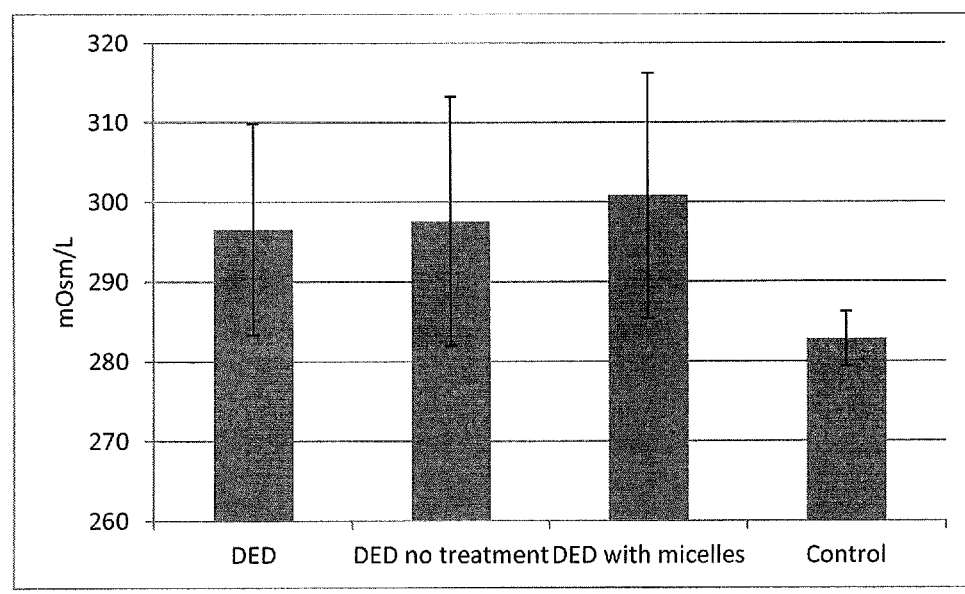
FIG. 11 graphically illustrates the effect of micelles on tear film osmolarity in vivo.

Tear osmolarity is often disregulated in DED. Similar to the previous example, tear film osmolarity measured on the TearLab osmometer shows no difference after treatment with micelles (FIG. 11).

Figure 12:
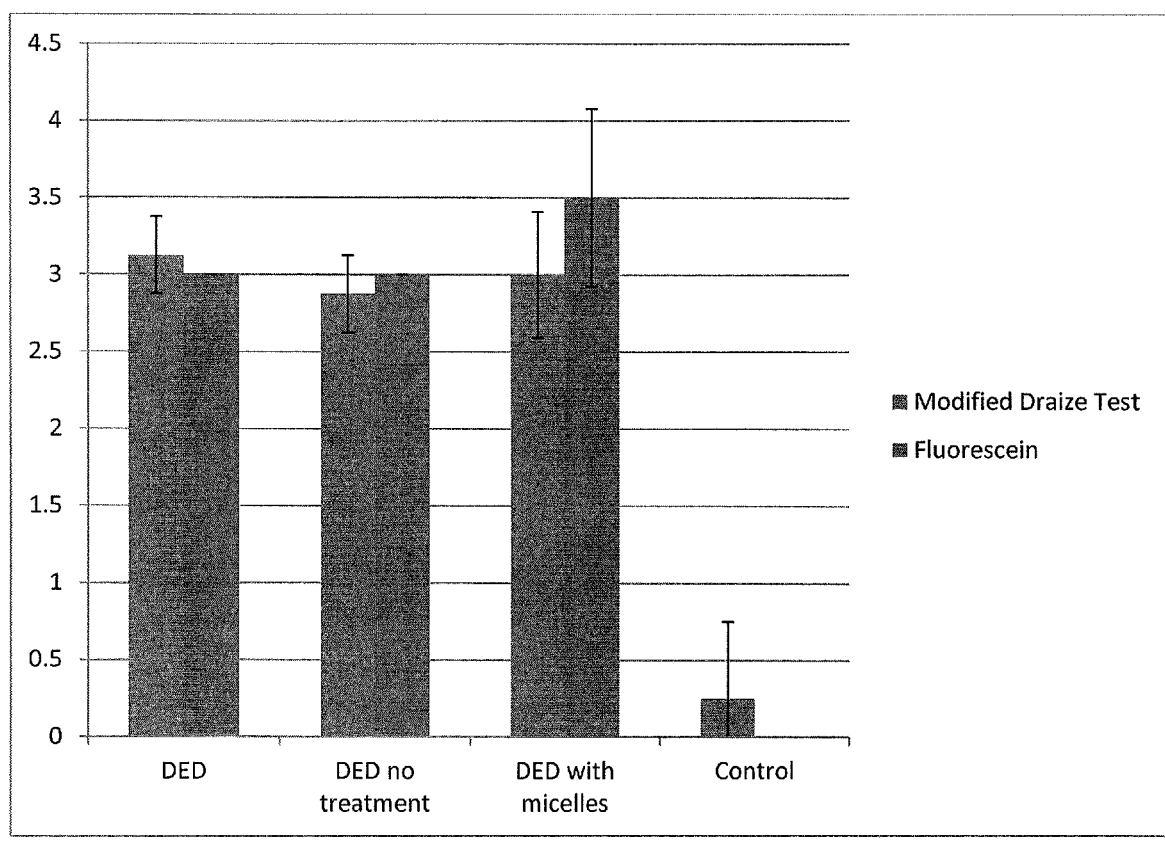
FIG. 12 illustrates that micelles have no adverse effect using modified Draize and fluorescein scoring.

Ophthalmologists use a variety of semi-quantitative scoring systems to assess the severity of ocular injury or disease, including (a) the Draize test, and (b) a fluorometric test in which fluorescein stains damaged corneal tissues thereby making them more visible under blue light. The higher the number, the greater the ocular tissues are damaged. Again, similar to above, a modified Draize and fluorescein scoring shows micelles have no adverse effect (FIG. 12).

The invention claimed is:

1. Biocompatible mucoadhesive block copolymer micelles comprising a degradable hydrophobic component, a degradable synthetic hydrophilic component and a mucoadhesive component that copolymerizes with the hydrophilic component, wherein the hydrophilic component comprises monomers selected from the group consisting of methacrylic acid, acrylic acid, hydroxyethyl methacrylate, hydroxypropylmethacrylamide, hydroxyethyl acrylate, polyethylene glycol methacrylate, vinyl, alcohol, vinylpyrollidone and mixtures thereof, and the block copolymer is prepared from the hydrophobic, hydrophilic and mucoadhesive components to yield block copolymer from which the micelles are prepared having a hydrophobic core and a hydrophilic shell incorporating the mucoadhesive component.

2. The micelles of claim 1, wherein the hydrophobic polymer is selected from the group consisting of polyesters, polyurethanes, polyureas, polycarbonates, polyethers, polysulfides, polysulfonates, polyimides, polybenzimidazoles, a lipoglycan, a proteoglycan and combinations thereof.

3. The micelles of claim 1, wherein the hydrophobic polymer is a polylactide, polyglycolide, poly(lactide-co-glycolide, poly(ε-caprolactone), poly-3-hydroxybutyrate, poly(dioxanone), poly(3-hydroxybutyrate), poly(3-hydroxyvalcrate), poly(valcrolactone), poly(tartonic acid), poly(malonic acid), poly(anhydrides), poly(orthoesters), polyphosphazenes and acryloyloxy dimethyl-γ-butyrolactone (DBA) or a combination thereof.

4. The micelles of claim 1, wherein the the hydrophilic and mucoadhesive components are polymerized using reversible addition-fragmentation chain transfer (RAFT) polymerization or free radical polymerization.

5. The micelles of claim 1, wherein the mucoadhesive component is selected from the group consisting of a boronic acid or derivative thereof, a thiol-containing compound, an acrylate, chitosan, cellulose, thiolated chitosan, thiolated hyaluronic acid, thiolated poly(acrylic) acid and mixtures thereof.

6. The micelles of claim 5, wherein the mucoadhesive component is a boronic acid or a boronic ester.

7. The micelles of claim 6, wherein the boronic acid or derivative thereof is selected from the group consisting of phenylboronic acid, 2-thienylboronic acid, methylboronic acid, cis-propenylboronic acid, trans-propenylboronic acid, (4-allylaminocarbonyl)benzeneboronic acid, (4-aminosulfonylphenyl)boronic acid, (4-benzyloxy-2-formyl)phenylboronic acid, (4-hydroxy-2-methyl)phenylboronic acid, (4-hydroxy-2-methyl)phenylboronic acid, (4-methanesulfonylaminomethylphenyl)boronic acid, (4-methanesulfonylaminomethylphenyl)boronic acid, (4-methylaminosulfonyl-phenyl)boronic acid, (4-methylaminosulfonylphenyl)boronic acid, (4-phenylamino-carbonylphenyl)boronic acid, (4-phenylaminocarbonylphenyl)boronic acid, (4-sec-butyl) benzeneboronic acid, (2,6-dimethoxy-4-methylphenyl)boronic acid, (2,6-dimethoxy-4-methylphenyl)boronic acid, (2-methylpropyl)boronic acid, (2-methylpropyl) boronic acid, (3-acetamido-5-carboxy)phenylboronic acid, (3-acetamido-5-carboxy) phenyl boronic acid, (3-acetamidomethylphenyl)boronic acid, (3-acetamidomethylphenyl) boronic acid, (3-allylaminocarbonyl)benzeneboronic acid, (3-cyanomethylphenyl)boronic acid, allylboronic acid pinacol ester, phenyl boronic acid trimethylene glycol ester, diisopropoxymethylborane, bis(hexyleneglycolato)diboron, t-butyl-N-[4-(4,4,5,5-tetramethyl-1,3,2-dioxaborolan-2-yl)phenyl]carbamate, 2,6-dimethyl-4-(4,4,5,5-tetramethyl1,3,2-dioxaborolan-2-yl) benzoate, 4-(4,4,5,5-tetramethyl1,3,2-dioxaborolan-2-yl) aniline, 4-(4,4,5,5-tetramethyl1,3,2-dioxaborolan-2-yl) benzoic acid, 4-(4,4,5,5-tetramethyl1,3,2-dioxaborolan-2-yl)phenol and 2-methoxy-4-(4,4,5,5-tetramethyl1,3,2-dioxaborolan-2-yl)phenol.

8. The micelles of claim 1, wherein the ratio of hydrophilic polymer:mucoadhesive is in the range of about 94.5:5 to about 65:30.

9. The micelles of claim 1, which are less than 200 nm in size.

10. The micelles of claim 1, loaded with cargo.

11. The micelles of claim 10, wherein the cargo comprises about 5-50% by weight of the micelles.

12. The micelles of claim 10, wherein the cargo is selected from a therapeutic agent and a diagnostic agent.

13. The micelles of claim 10, wherein the cargo is selected from the group consisting of analgesics, anti-inflammatory agents, anti-pathogenic agents including antibacterial, antiviral and antifungal agents, gastrointestinal agents, antihistamines, anti-allergic agents, anti-cancer agents, anti-nauseants, anti-asthmatic agents, decongestants, glaucoma medication, intra-ocular pressure lowering drugs (IOP-lowering agents), lubricants, demulcents, counter-irritants, hypertonic tears, anti-ototoxic agents, proteins, nucleic acids and carbohydrates.

14. The micelles of claim 10, wherein the cargo is an ophthalmic drug.

15. The micelles of claim 14, wherein the ophthalmic drug is selected from the group consisting of cyclosporine A, acyclovir, atropine, acetazolamide, alphagan, azithromycin, bacitracin, betadine, betaxolol, betoptic, brinzolamide, carbachol, cefazolin, celluvisc, chloramphenicol, ciloxan, ciprofloxacin, cephalosporin, emecarium, dexamethasone, dipivefrin, dorzolamide, epinephrine, erythromycin, fluorescein, flurbiprofen, quinolones such as fluoroquinolone, gentamicin, goniosol, gramicidin, gancyclovir, gatafloxacin, humorsol, hylartin, itraconazole, ketotifen, latanoprost, levofloxacin, bimatoprost, travoprost, pilocarpine, polymyxin B, prednisolone, proparacaine, propine, puralube, mannitol, methazolamide, miconazole, miostat, moxifloxacin, natamycin, neomycin, neptazane, ocuflox, ofloxacin, oxytetracycline, olopatadine, phenylephrine, prostaglandin, sodium hyaluronate, suprofen, terramycin, timolol, tobramycin, triamcinolone, trfluridine, tropicamide, vidarabine, valcyclovir, vancomycin, xalatan, phenylephrine, a prostaglandin and an anti-VEGF drug.

16. A composition comprising the micelles of claim 1 combined with a pharmaceutically acceptable carrier.

17. The composition of claim 16, is formulated for oral, intranasal, enteral, topical, sublingual, intra-arterial, intramedullary, intrauterine, intrathecal, inhalation, ocular, transdermal, vaginal, rectal, subcutaneous, intraperitoneal, intramuscular or intravenous administration.

18. The composition of claim 16, formulated for topical administration to the eye or ear.

19. A method of delivering cargo to a mucosal surface in a mammal comprising administering to the mammal micelles as defined in claim 10.

20. The method of claim 19, to treat or diagnose a pathogenic condition affecting the eye, nose, mouth, ear, throat, esophagus, stomach, intestines, endometrium, penis, vagina or anus.

21. The method of claim 20, wherein the pathogenic condition is infection, inflammation, cancer, degenerative disease, allergic reaction or mechanical injury.

22. The method of claim 19, wherein the cargo is selected from the group consisting of analgesics, anti-inflammatory agents, anti-pathogenic agents including antibacterial, antiviral and antifungal agents, gastrointestinal agents, antihistamines, anti-allergic agents, anti-cancer agents, antinauseants, anti-asthmatic agents, decongestants, glaucoma medication, intra-ocular pressure lowering drugs (IOP-lowering agents), lubricants, demulcents, counter-irritants, hypertonic tears, anti-ototoxic agents, proteins, nucleic acids and carbohydrates.

23. The method of claim 19, wherein the cargo is an ophthalmic drug.

24. A mucoadhesive-based ophthalmic drug delivery system comprising poly(L-lactide)-b-poly(methacrylic acid-co-acrylamidophenylboronic acid) copolymer micelles.

25. The drug delivery system of claim 24, additionally comprising an ophthalmic drug.

26. The drug delivery system of claim 25, wherein the ophthalmic drug is selected from the group consisting of cyclosporine A, acyclovir, atropine, acetazolamide, alphagan, azithromycin, bacitracin, betadine, betaxolol, betoptic, brinzolamide, carbachol, cefazolin, celluvisc, chloramphenicol, ciloxan, ciprofloxacin, cephalosporin, emecarium, dexamethasone, dipivefrin, dorzolamide, epinephrine, erythromycin, fluorescein, flurbiprofen, quinolones such as fluoroquinolone, gentamicin, goniosol, gramicidin, gancyclovir, gatafloxacin, humorsol, hylartin, itraconazole, ketotifen, latanoprost, levofloxacin, bimatoprost, travoprost, pilocarpine, polymyxin B, prednisolone, proparacaine, propine, puralube, mannitol, methazolamide, miconazole, miostat, moxifloxacin, natamycin, neomycin, neptazane, ocuflox, ofloxacin, oxytetracycline, olopatadine, phenylephrine, prostaglandin, sodium hyaluronate, suprofen, terramycin, timolol, tobramycin, triamcinolone, trfluridine, tropicamide, vidarabine, valcyclovir, vancomycin, xalatan, phenylephrine, a prostaglandin and an anti-VEGF drug.

27. The drug delivery system of claim 25, wherein the ophthalmic drug is cyclosporine A.

\* \* \* \* \*